(12) United States Patent
Belcheva et al.

(10) Patent No.: US 9,517,067 B2
(45) Date of Patent: *Dec. 13, 2016

(54) SYSTEM AND METHOD FOR SATELLITE DRUG DELIVERY

(71) Applicant: Covidien LP, Mansfield, MA (US)

(72) Inventors: Nadya D. Belcheva, Essex Junction, VT (US); Joshua Stopek, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/530,853

(22) Filed: Nov. 3, 2014

(65) Prior Publication Data
US 2015/0051540 A1 Feb. 19, 2015

Related U.S. Application Data

(63) Continuation of application No. 12/910,036, filed on Nov. 29, 2010, now Pat. No. 8,900,616.

(51) Int. Cl.

| | | |
|---|---|---|
| A61K 9/00 | (2006.01) | |
| A61J 3/00 | (2006.01) | |
| A61B 17/064 | (2006.01) | |
| A61B 17/10 | (2006.01) | |
| A61L 27/54 | (2006.01) | |
| A61B 17/068 | (2006.01) | |
| A61M 37/00 | (2006.01) | |
| A61L 31/16 | (2006.01) | |
| A61L 17/00 | (2006.01) | |
| A61B 17/072 | (2006.01) | |
| A61B 17/00 | (2006.01) | |

(52) U.S. Cl.
CPC ......... *A61B 17/0684* (2013.01); *A61K 9/0024* (2013.01); *A61L 17/005* (2013.01); *A61L 27/54* (2013.01); *A61L 31/16* (2013.01); *A61M 37/00* (2013.01); *A61B 17/0682* (2013.01); *A61B 17/072* (2013.01); *A61B 2017/00004* (2013.01); *A61B 2017/00893* (2013.01); *A61B 2090/3991* (2016.02); *A61L 2300/402* (2013.01); *A61L 2300/404* (2013.01); *A61L 2300/416* (2013.01); *A61L 2300/42* (2013.01)

(58) Field of Classification Search
None
See application file for complete search history.

(56) References Cited

U.S. PATENT DOCUMENTS

| | | |
|---|---|---|
| 4,450,150 A | 5/1984 | Sidman |
| 4,597,753 A | 7/1986 | Turley |
| 4,670,014 A | 6/1987 | Huc et al. |
| 4,674,480 A | 6/1987 | Lemelson |
| 5,035,891 A | 7/1991 | Runkel et al. |
| 5,174,487 A | 12/1992 | Rothfuss et al. |
| 5,397,324 A | 3/1995 | Carroll et al. |
| 5,441,193 A | 8/1995 | Gravener |
| 5,497,933 A | 3/1996 | DeFonzo et al. |
| 5,542,594 A | 8/1996 | McKean et al. |
| 5,702,409 A | 12/1997 | Rayburn et al. |
| 5,728,107 A | 3/1998 | Zlock et al. |
| 5,758,814 A | 6/1998 | Gallagher et al. |
| 5,769,892 A | 6/1998 | Kingwell |
| 6,045,560 A | 4/2000 | McKean et al. |
| 6,503,257 B2 | 1/2003 | Grant et al. |
| 6,869,436 B2 | 3/2005 | Wendlandt |
| 7,083,648 B2 | 8/2006 | Yu et al. |
| 7,226,467 B2 | 6/2007 | Lucatero et al. |
| 7,431,730 B2 | 10/2008 | Viola |
| 7,438,209 B1 | 10/2008 | Hess et al. |
| 7,455,682 B2 | 11/2008 | Viola |
| 7,547,312 B2 | 6/2009 | Bauman et al. |
| 7,635,073 B2 | 12/2009 | Heinrich |
| 7,665,646 B2 | 2/2010 | Prommersberger |
| 7,669,747 B2 | 3/2010 | Weisenburgh, II et al. |
| 7,673,782 B2 | 3/2010 | Hess et al. |
| 7,845,536 B2 | 12/2010 | Viola et al. |
| 8,579,920 B2 * | 11/2013 | Nering ............... A61B 17/0682 606/143 |
| 8,900,616 B2 | 12/2014 | Belcheva et al. |
| 2004/0232201 A1 | 11/2004 | Wenchell et al. |
| 2004/0260386 A1 | 12/2004 | Shalaby |
| 2005/0059997 A1 | 3/2005 | Bauman et al. |
| 2005/0145671 A1 | 7/2005 | Viola |
| 2005/0184121 A1 | 8/2005 | Heinrich |
| 2005/0192628 A1 | 9/2005 | Viola |
| 2006/0079913 A1 | 4/2006 | Whitfield et al. |
| 2006/0085032 A1 | 4/2006 | Viola |
| 2006/0085033 A1 | 4/2006 | Criscuolo et al. |
| 2006/0108393 A1 | 5/2006 | Heinrich et al. |

(Continued)

FOREIGN PATENT DOCUMENTS

| | | |
|---|---|---|
| EP | 0531742 A1 | 3/1993 |
| EP | 1 815 804 A2 | 8/2007 |
| EP | 1844734 A2 | 10/2007 |
| WO | 2007/015971 A2 | 2/2007 |

OTHER PUBLICATIONS

European Search Report No. 11250759.5 dated Oct. 1, 2014.

*Primary Examiner* — Abigail Fisher

(57) ABSTRACT

The present disclosure is directed to an implantable repository including a housing comprising at least one bioactive agent and at least one attachment member coupled to the housing, the at least one attachment member configured to couple the implantable repository to at least one of a medical device and a tissue surface.

15 Claims, 13 Drawing Sheets

(56) References Cited

U.S. PATENT DOCUMENTS

| | | |
|---|---|---|
| 2006/0206124 A1 | 9/2006 | Milliman et al. |
| 2006/0235469 A1 | 10/2006 | Viola |
| 2006/0271104 A1 | 11/2006 | Viola et al. |
| 2007/0179528 A1 | 8/2007 | Soltz et al. |
| 2007/0225761 A1* | 9/2007 | Shetty .............. A61B 17/06166 606/219 |
| 2007/0243228 A1 | 10/2007 | McKay |
| 2008/0058869 A1 | 3/2008 | Stopek et al. |
| 2008/0078808 A1 | 4/2008 | Hess et al. |
| 2008/0110958 A1 | 5/2008 | McKenna et al. |
| 2008/0110961 A1 | 5/2008 | Voegele et al. |
| 2008/0140115 A1 | 6/2008 | Stopek |
| 2008/0230583 A1 | 9/2008 | Heinrich |
| 2008/0287987 A1 | 11/2008 | Boyden et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001122 A1 | 1/2009 | Prommersberger et al. |
| 2009/0001125 A1 | 1/2009 | Hess et al. |
| 2009/0001128 A1 | 1/2009 | Weisenburgh, II et al. |
| 2009/0001130 A1 | 1/2009 | Hess et al. |
| 2009/0050670 A1 | 2/2009 | Viola |
| 2009/0062922 A1 | 3/2009 | McKay |
| 2009/0076588 A1 | 3/2009 | Weber |
| 2009/0112236 A1 | 4/2009 | Stopek |
| 2009/0130162 A2 | 5/2009 | Pathak et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2010/0012703 A1 | 1/2010 | Calabrese et al. |
| 2010/0059570 A1 | 3/2010 | Ostapoff et al. |
| 2010/0087840 A1 | 4/2010 | Ebersole et al. |
| 2010/0198257 A1 | 8/2010 | Stopek et al. |
| 2011/0129512 A1 | 6/2011 | Roby et al. |

* cited by examiner

SYSTEM AND METHOD FOR SATELLITE DRUG DELIVERY

CROSS-REFERENCE TO RELATED APPLICATIONS

This present application is a continuation application of U.S. patent application Ser. No. 12/910,036, filed on Nov. 29, 2010, the entire contents of which are hereby incorporated by reference herein.

BACKGROUND

Administration of bioactive agents in conjunction with medical procedures is common practice in the surgical arts. Bioactive agents have been applied during procedures as solutions sprayed onto tissue or as coatings on medical devices.

Use of bioactive agents during surgical procedures allows for local application of medicaments. This may enable the use of bioactive agents that may not be absorbed when administered orally or parenterally. Hemostatic agents may be used to reduce bleeding in situ, analgesics may be applied to the injured tissue, antibiotics may be used to prevent infection at the site of incision, and anti-adhesion agents may prevent scar tissue formation around an implant.

Processes used to attach bioactive agents to a medical device, such as surface modification by methods such as plasma treatment, silane coupling treatment and acid sensitization, cell immobilization, plasma grafting, and the like are often complicated and costly. Often bioactive agents may be applied as a coating to specific medical devices. Therefore, other devices at the tissue site may not benefit from local delivery of a bioactive agent from the coated medical device.

SUMMARY

The present disclosure provides for an implantable repository including a housing comprising at least one bioactive agent and at least one attachment member coupled to the housing, the at least one attachment member configured to couple the implantable repository to at least one of a medical device and a tissue surface.

The present disclosure also provides for an implantable repository including a housing defining at least one lumen therein, the lumen including at least one bioactive agent disposed therein; and at least one attachment member coupled to the housing, the at least one attachment member configured to couple the implantable repository to at least one of a medical device and a tissue surface.

The present disclosure also provides for a method including depositing at least one implantable repository on a tissue surface, the at least one implantable repository including a housing having at least one attachment member coupled thereto and at least one bioactive agent; and securing the at least one implantable repository on the tissue surface by coupling the at least one attachment member to at least one wound closure device configured to penetrate the tissue surface.

In certain embodiments, an instrument is disclosed comprising an elongated housing having a proximal end and a distal end; a handle assembly at the proximal end of the elongated housing; and an end effector assembly disposed at the distal end of the elongated housing. The end effector assembly includes a plurality of fasteners, at least one implantable repository, a cartridge assembly, and an anvil assembly. The at least one implantable repository may be coupled to at least one of the cartridge assembly or the anvil assembly.

Alternatively, a surgical stapling instrument is disclosed comprising an elongated body portion; a tool assembly supported on a distal end of the elongated body portion, the tool assembly including a plurality of fasteners, an anvil assembly and a cartridge assembly, a repository support assembly selectively engageable with at least one of the anvil assembly and the cal Lidge assembly, the repository support assembly including a support member, a working surface, and at least one implantable repository disposed on the working surface and in a firing path of the plurality of fasteners, such that the plurality of fasteners are fired to penetrate tissue and to attach the at least one implantable repository thereto.

Methods for depositing the implantable repository on a tissue surface are also disclosed.

BRIEF DESCRIPTION OF DRAWINGS

The foregoing objects and advantages of the disclosure will become more apparent from the reading of the following description in connection with the accompanying drawings, in which.

DETAILED DESCRIPTION

Figure 1A:
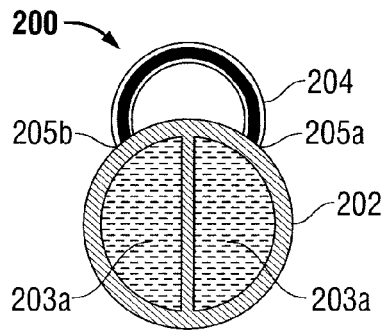
FIG. 1A is a perspective view of an implantable repository according to an embodiment of the disclosure.

The present disclosure provides for an implantable repository for delivering a bioactive agent to tissue and methods of using the same. The present disclosure further allows for use of any bioactive agent or group of bioactive agents with various types of wound closure devices.

In accordance with the present disclosure, an implantable repository may be a part of a satellite drug delivery system (SDDS). In embodiments, the SDDS may include a repository, a receptacle, a capsule or any other suitable repository having a housing. The housing of the implantable repositories may include a bioactive agent contained or embedded within the housing. The repository may also include an attachment member such as a loop or a hook coupled to or extending from the housing. Medical instruments for delivering the repositories are also provided. The implantable repositories may also be coupled via a medical device, e.g., a fastener, which may couple to the attachment member for transport and/or attachment to tissue.

The term "wound closure device" refers to any device suitable for joining together two or more tissue structures, such as sutures, adhesives, staples, clips, fasteners, tacks, and the like. The term "medical device" refers to any structure formed of a biocompatible material that is suitable for being attached or implanted into tissue, body organs or lumens, including, but not limited to, wound closure devices, films, foams, sheets, pledgets, tissue grafts (e.g., vascular, skin, bone, etc.), stents, scaffolds, meshes, buttresses, and the like. In the drawings and in the description that follows, the term "proximal," refers to an end of an instrument that is closer to the user, while the term "distal" refers to the end of the instrument that is further from the user.

Referring now in specific detail to the drawings, in which like numbers identify similar or identical elements, an implantable repository is depicted in FIGS. 1A-E. Turning to FIG. 1A, an implantable repository 200 includes a housing 202 defining one or more lumens 203a therein and an attachment member 204. The attachment member 204 is illustrated as a loop attached at both ends thereof 205a, 205b to the housing 202. In embodiments, one of the ends 205a, 205b of the attachment member 204 may be detachable, allowing for the attachment member 204 to operate as a latch and to be coupled to the housing 202 after attachment of the implantable repository 200. The detachable end of the attachment member 204 may additionally be configured for piercing tissue and other medical devices.

The implantable repository 200 may be a biodegradable capsule or any other suitable container having a bioactive agent disposed within the housing 202, namely, within the lumen 203. In embodiments, the bioactive agent may also be included within the housing 202 itself and may be absorbed into the tissue as the housing 202 is degraded. Examples of biodegradable materials and bioactive agents are discussed in more detail below.

Figure 1B:
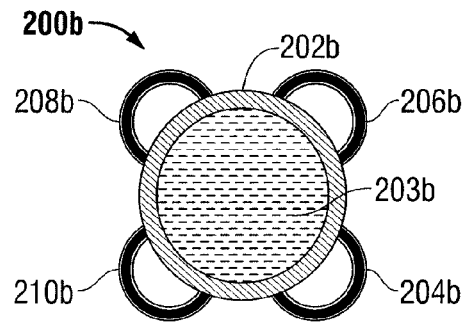
FIG. 1B is a perspective view of an implantable repository according to an embodiment of the disclosure.
Figure 1C:
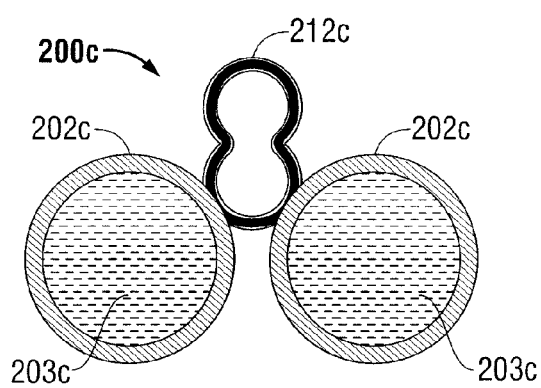
FIG. 1C is a perspective view of an implantable repository according to an embodiment of the disclosure.
Figure 1D:
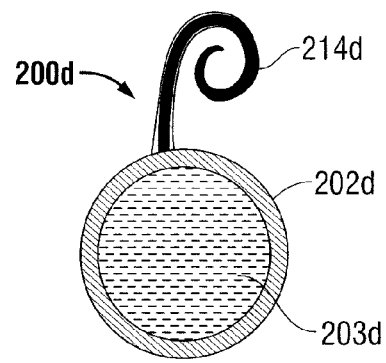
FIG. 1D is a perspective view of an implantable repository according to an embodiment of the disclosure.
Figure 1E:
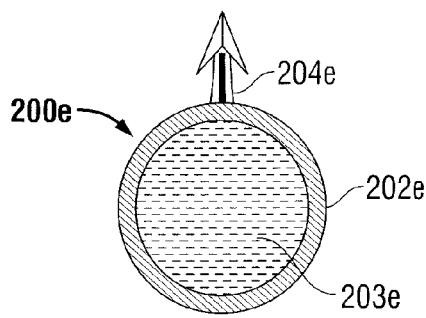
FIG. 1E is a perspective view of an implantable repository according to an embodiment of the disclosure.

As shown in FIG. 1B the repository 200b may also include multiple attachment members 204b, 206b, 208b, and 210b, which may be the same or different in size and shape, attached to a single housing 202b having a lumen 203b defined therein. In other embodiments, as shown in FIG. 1C, multiple repository housings 202c, each having a lumen 203c defined therein, may be attached to a single attachment member 212c. As shown in FIG. 1D, the attachment member 214d may be hook-shaped and may also be coupled to a housing 202d having a lumen 203d defined therein. In embodiments, the attachment members (e.g., attachment members 204, 204b, 212c, 214d) may be formed from a biodegradable suture. As shown in FIG. 1E, an attachment member 204e may be a barb-shaped implement configured for piercing tissue and other medical devices and may also be coupled to a housing 202e having a lumen 203e defined therein.

Figure 2C:
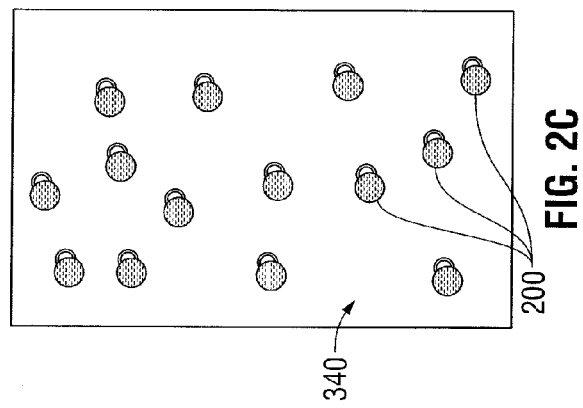
FIGS. 2C and 2D illustrate a plurality of implantable repositories attached to a tissue buttress according to an embodiment of the disclosure.
Figure 2D:
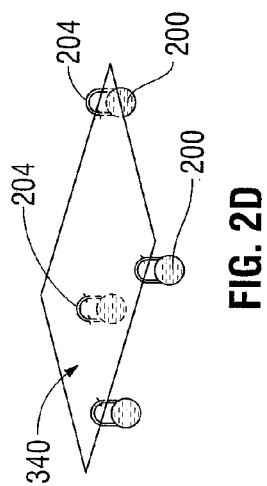
Figure 2A:
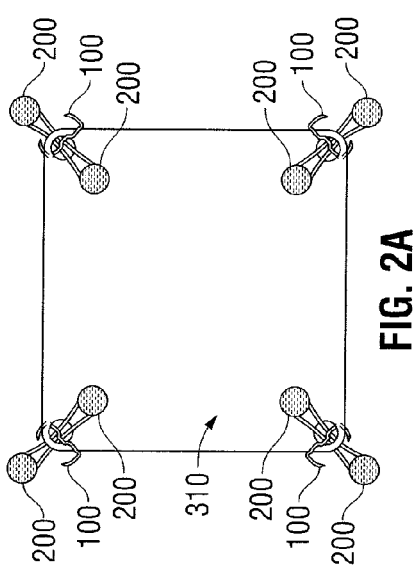
FIG. 2A illustrates a plurality of implantable repositories attached to a medical device according to an embodiment of the disclosure.
Figure 2B:
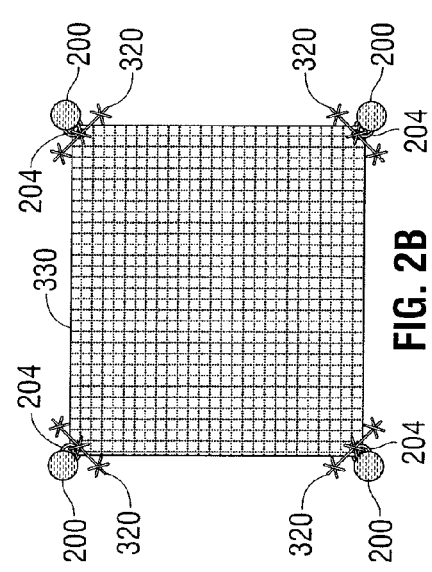
FIG. 2B illustrates a plurality of implantable repositories attached to a mesh according to an embodiment of the disclosure.

FIGS. 2A-D depict the implant capsules or repositories 200 attached to a medical device 310 and/or tissue. The implantable repositories 200 may be attached using a fastener 100, as shown in FIG. 2A. In other embodiments, a wound closure device such as a suture 320, in embodiments a barbed suture, may be attached by threading the suture through the attachment member 204 of the implantable repository 200 and to a medical device 330 (e.g., mesh), as depicted in FIG. 2B. In other embodiments, as depicted in FIG. 2C, the implantable repository 200 may be attached to a tissue buttress or other implant 340 with an internal adhesive or glue directly on the surface thereof FIG. 2D illustrates an implant 340 having several repositories 200 pierced therethrough. More specifically, the attachment members 204 have pierced the implant 340, attaching the repositories 204 to the implant 340. In some embodiments, the repositories may be attached to medical devices. For example, a suture may be threaded through the repositories or through the attachment members. Once repositories are positioned on the sutures, a user may then suture tissue, attaching the repositories to the tissue surface.

In other embodiments, the repositories may be attached directly to a tissue surface (e.g., an adhesive). The repository may include biodegradable and/or non-biodegradable materials, which are adapted for releasing the bioactive agent in a controlled manner at the site of application as described in more detail below. Suitable materials, including biodegradable polymers, ceramics and metals, are within the purview of those skilled in the art.

Figure 3:
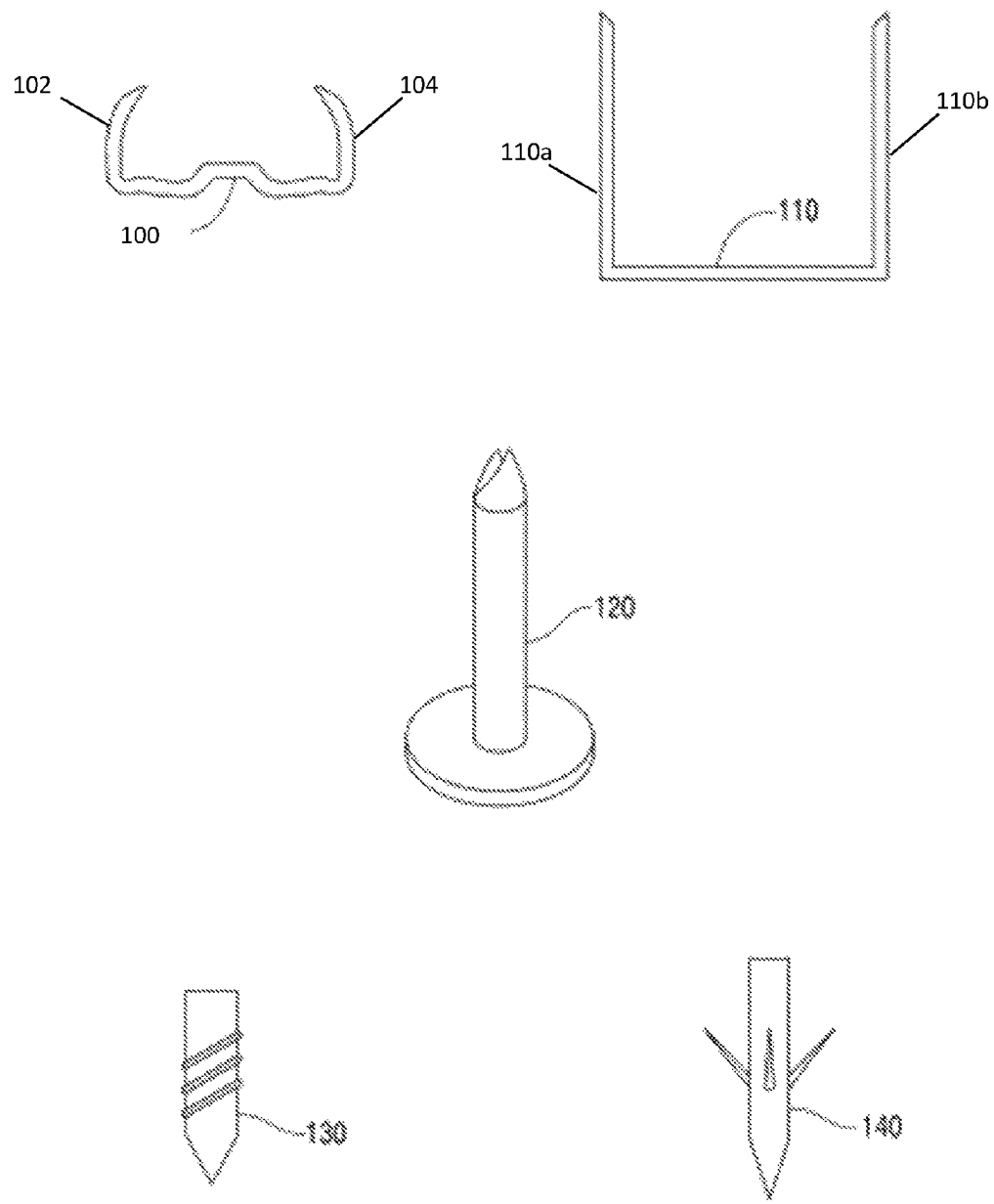
FIG. 3 illustrates fasteners for attaching the implantable repository according to an embodiment of the disclosure.

FIG. 3 depicts exemplary fasteners 100, 110, 120, 130, and 140 for securing repositories to tissue and/or other medical devices. The fastener may be, for example, a mandibular-type fastener 100, a staple 110, a tack 120, a screw 130, an anchor 140, and the like. The fasteners may be formed of any suitable absorbable or non-absorbable material. Another example of a suitable fastener is ABSORBATACK™ available from Tyco Health Group LP, doing business as Covidien (North Haven, Conn.).

Figure 4:
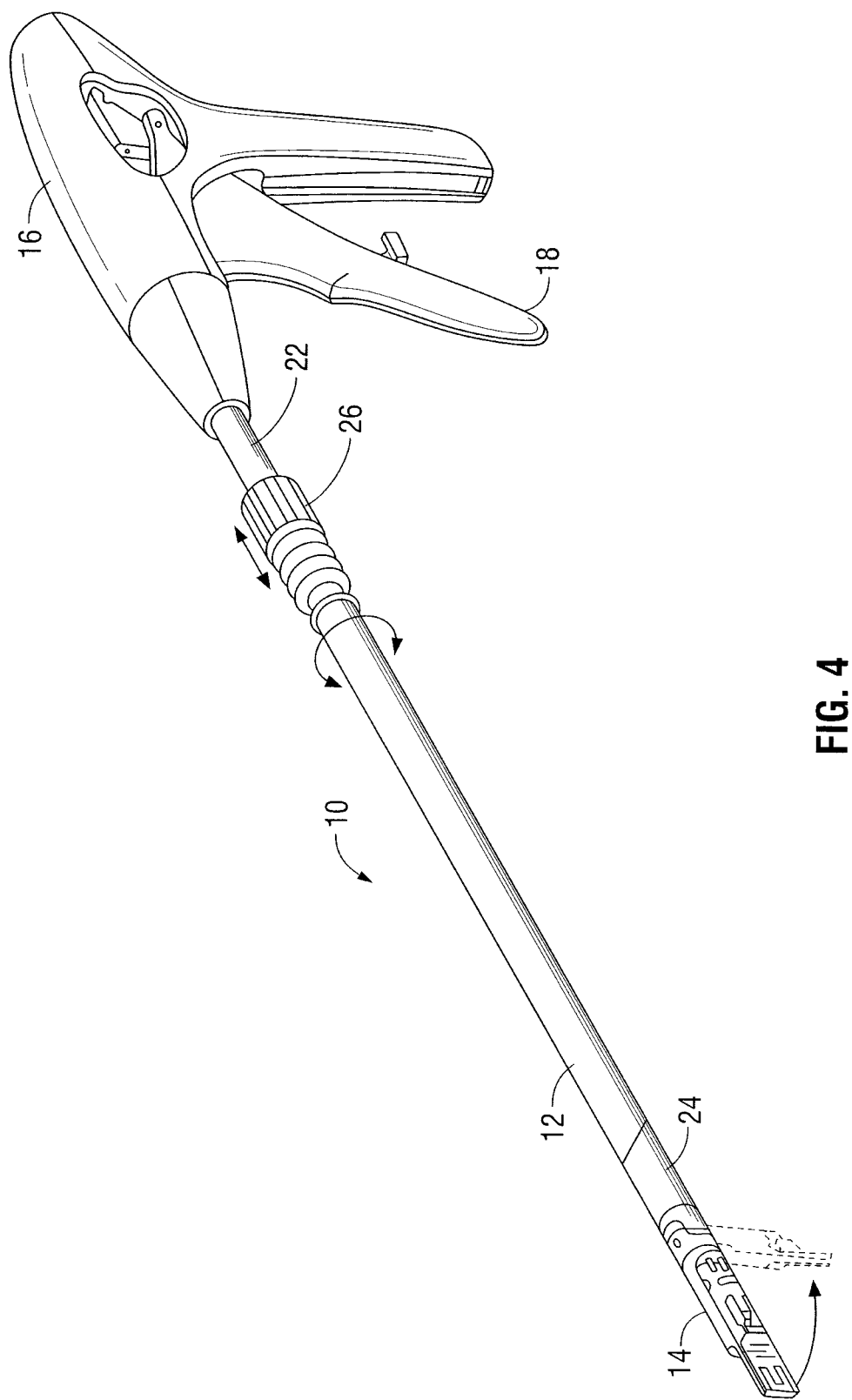
FIG. 4 is a perspective view of a medical instrument according to an embodiment of the disclosure.

FIG. 4 depicts a surgical instrument 10 for affixing a fastener and repository to tissue. The instrument 10 includes an elongated housing 12 having a proximal end 22 and a distal end 24. An end effector assembly 14 is disposed at the distal end 24 of elongated housing 12. In embodiments, the end effector assembly 14 may be removably mountable with the distal end 24 of the elongated housing 12. End effector assembly 14 is provided to house or retain a plurality of fasteners 100 (FIG. 5) and implantable repositories 200 (FIG. 5), in accordance with the present disclosure, for application to body tissue. Suitable fasteners 100 may include, but are not limited to, those shown in FIG. 3.

In embodiments, elongated housing 12 is dimensioned to fit through conventional cannula structures such as those used in hernia repair techniques. Elongated housing 12 includes a collar 26 rotatably connected to the handle assembly 16. A handle assembly 16 is located at proximal end 22 of elongated housing 12. The handle assembly 16 includes a trigger 18 operably connected to elongated housing 12 and the end effector assembly 14, enabling dispensing of fasteners 100 from the end effector assembly 14.

Figure 5:
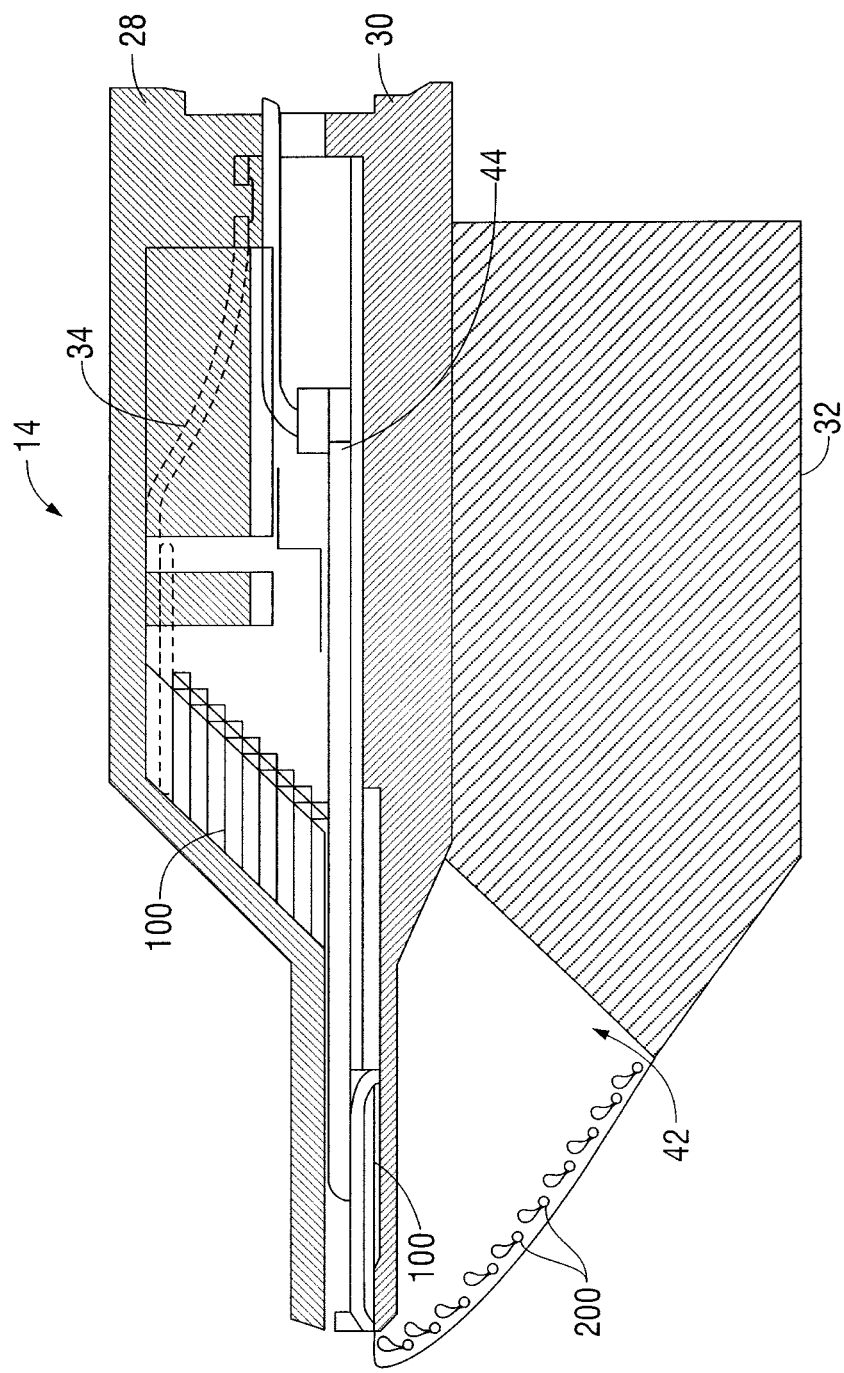
FIG. 5 is a side cross-sectional view of an end effector assembly of the medical instrument of FIG. 4.
Figure 6:
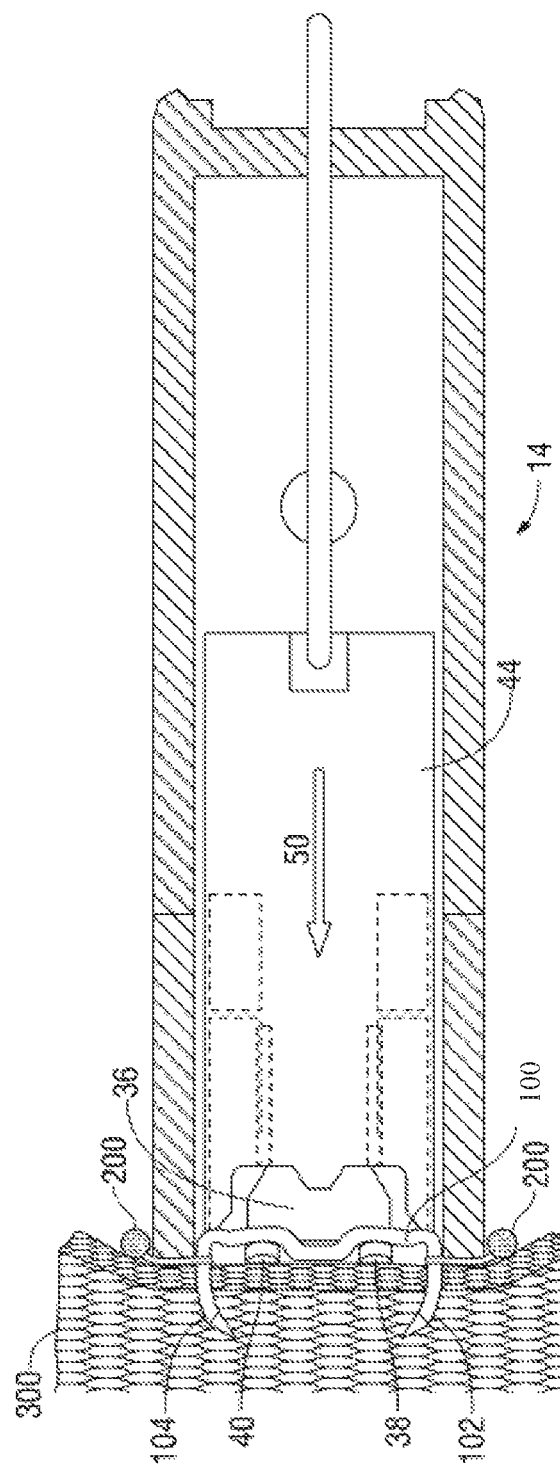
FIG. 6 is a top cross-sectional view of a distal end portion of the medical instrument of FIG. 4 shown in contact with tissue prior to firing of a fastener.

As shown in FIGS. 5 and 6, end effector assembly 14 includes a top housing 28, a divider wall 30, and a bottom housing 32. The bottom housing 32 may be removably attached to the divider wall 30. Between the top housing 28 and the divider wall 30, the end effector assembly 14 is adapted to contain a plurality of fasteners 100 which are shaped to transport and attach implantable repositories 200 to a medical device and/or tissue. Between the divider wall 30 and the bottom housing 32 is a cartridge 42 containing the implantable repositories 200. The cartridge 42 ejects the implantable repositories 200 in such a manner as to afford attachment of the implantable repository 200 to the fastener 100 prior to penetration and attachment to a medical device or tissue. In general, through the manipulation of trigger 18 (FIG. 4), a fastener 100 is joined to one or more implantable repositories 200 and ejected, out of the end effector assembly 14 and into tissue and/or medical devices.

As shown in FIG. 5, the fasteners 100 are positioned and retained by a resilient biasing member 34 having dual resilient legs whose side profile is curved. FIG. 6 depicts the fastener 100 and two implantable repositories 200 disposed on the fastener legs 102 and 104 of the fastener 100 upon initial insertion into tissue 300. The downward force of the biasing member 34 is evenly distributed over the lowermost fastener 100. An anvil assembly 36 (FIG. 6) includes upwardly extending feet 38 and 40, which form anvils at the distal end. The lowermost fastener 100 is in position for engagement by fastener pusher 44. Fastener pusher 44 moves in a direction shown by arrow 50. The fastener pusher 44 provides transmission of the advancing force on the fastener 100. Simultaneously, the cartridge 42 ejects the implantable repository 200 such that the fastener legs 102 and 104 of the fastener 100 encompass at least one implantable repository 200. In order to eject the implantable repository 200, the cartridge 42 may include a biasing and/or ejection mechanism. The complementary configuration of the fastener pusher 44 and the fastener 100 provides for uniform distribution of force as the fastener 100 is deformed about the anvil assembly 36 (FIG. 6).

Figure 7:
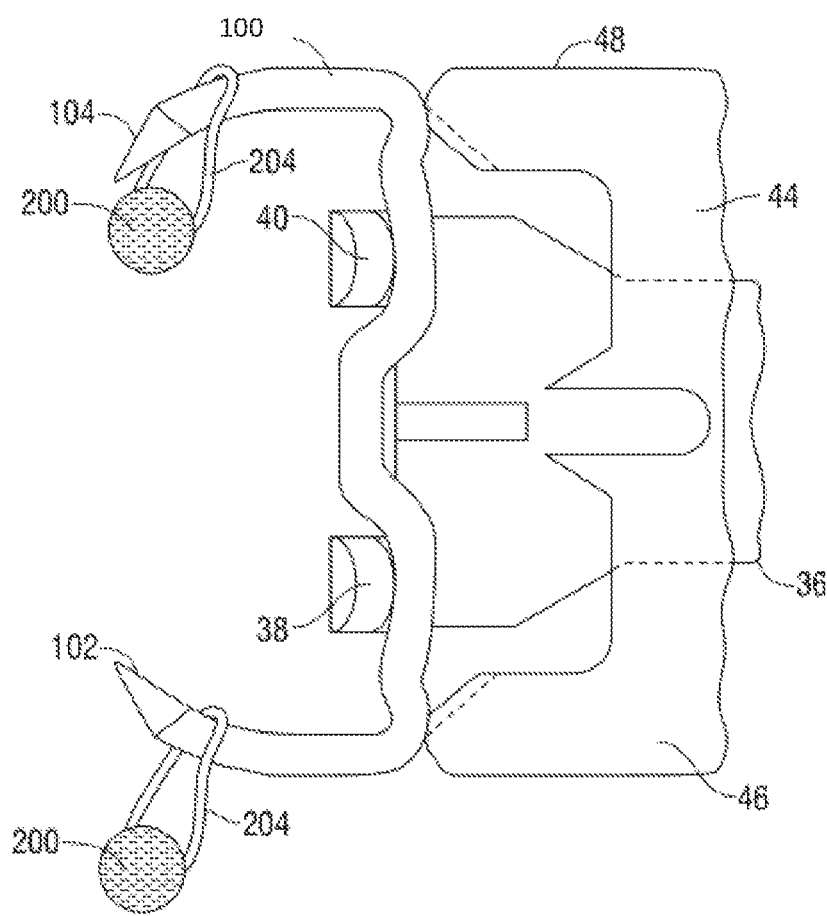
FIG. 7 is a top cross-sectional view of the distal end portion of the medical instrument of FIG. 4, contacting the fastener according to an embodiment of the disclosure.
Figure 8:
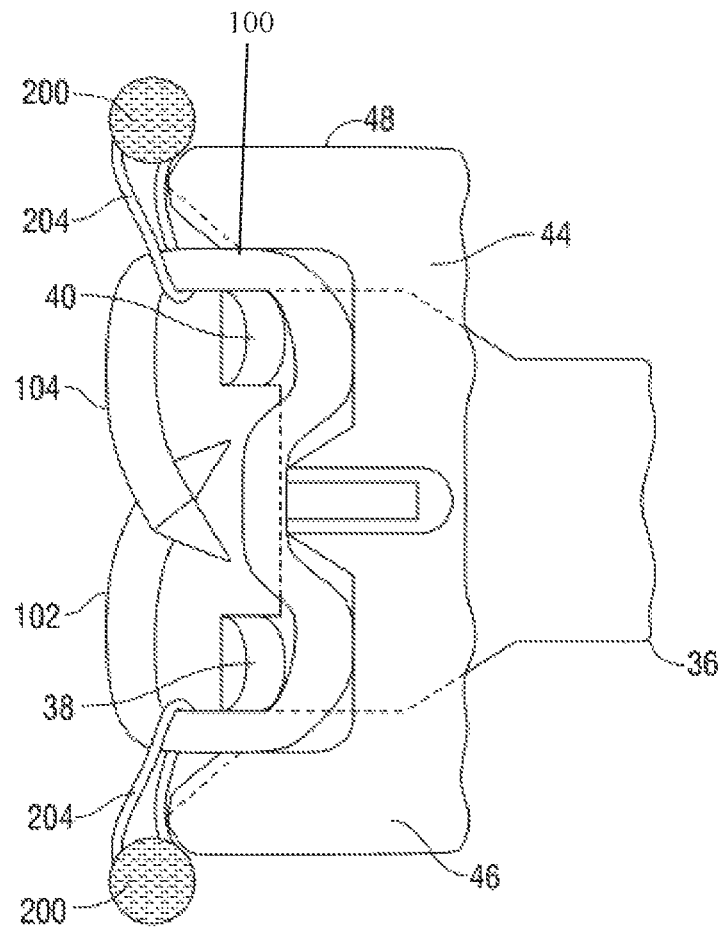
FIG. 8 is a top cross-sectional view of the distal end portion of the medical instrument of FIG. 4, forming the fastener according to an embodiment of the disclosure.

As shown in FIGS. 7 and 8, the fastener pusher 44 pushes the legs 102 and 104 of the fastener 100 against the anvil feet 38 and 40. The extensions 46 and 48 of the fastener pusher 44 surround a portion of the legs 102 and 104 of the fastener 100 causing the remaining portion of the legs 102 and 104 to pass through the attachment members 204 of the repositories 200 and to bow inward, securing the fastener 100 and implantable repositories 200 to tissue.

Figure 9:
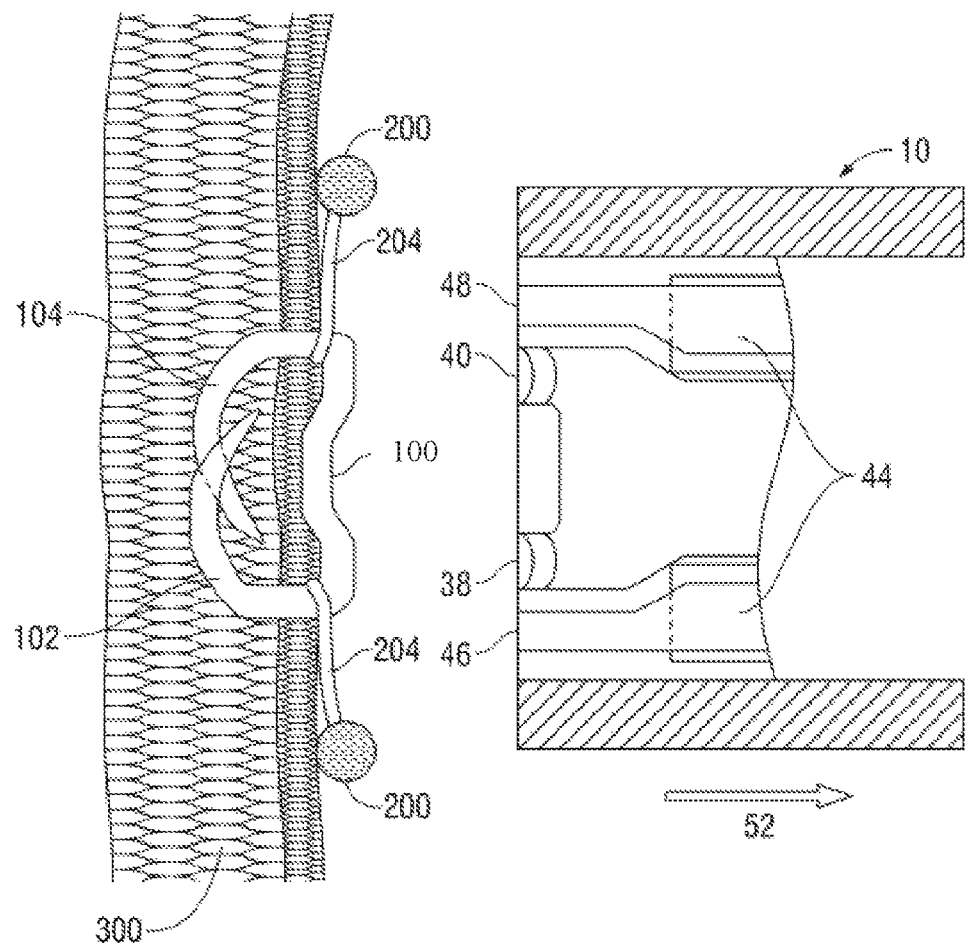
FIG. 9 is a top cross-sectional view illustrating the fastener and the implantable repository after closure about tissue according to an embodiment of the disclosure.

FIG. 9 depicts the extensions 46 and 48 of the fastener pusher 44, which cause the legs 102 and 104 of the fastener 100 to bow inward. Implantable repositories 200 are shown attached to the legs 102 and 104 of the fastener 100, the implantable repositories 200 may remain outside the tissue surface 300. In embodiments, the implantable repositories 200 may enter/penetrate the tissue surface with the legs 102 and 104. Arrow 52 indicates the direction of movement of the medical instrument 10.

Figure 10:
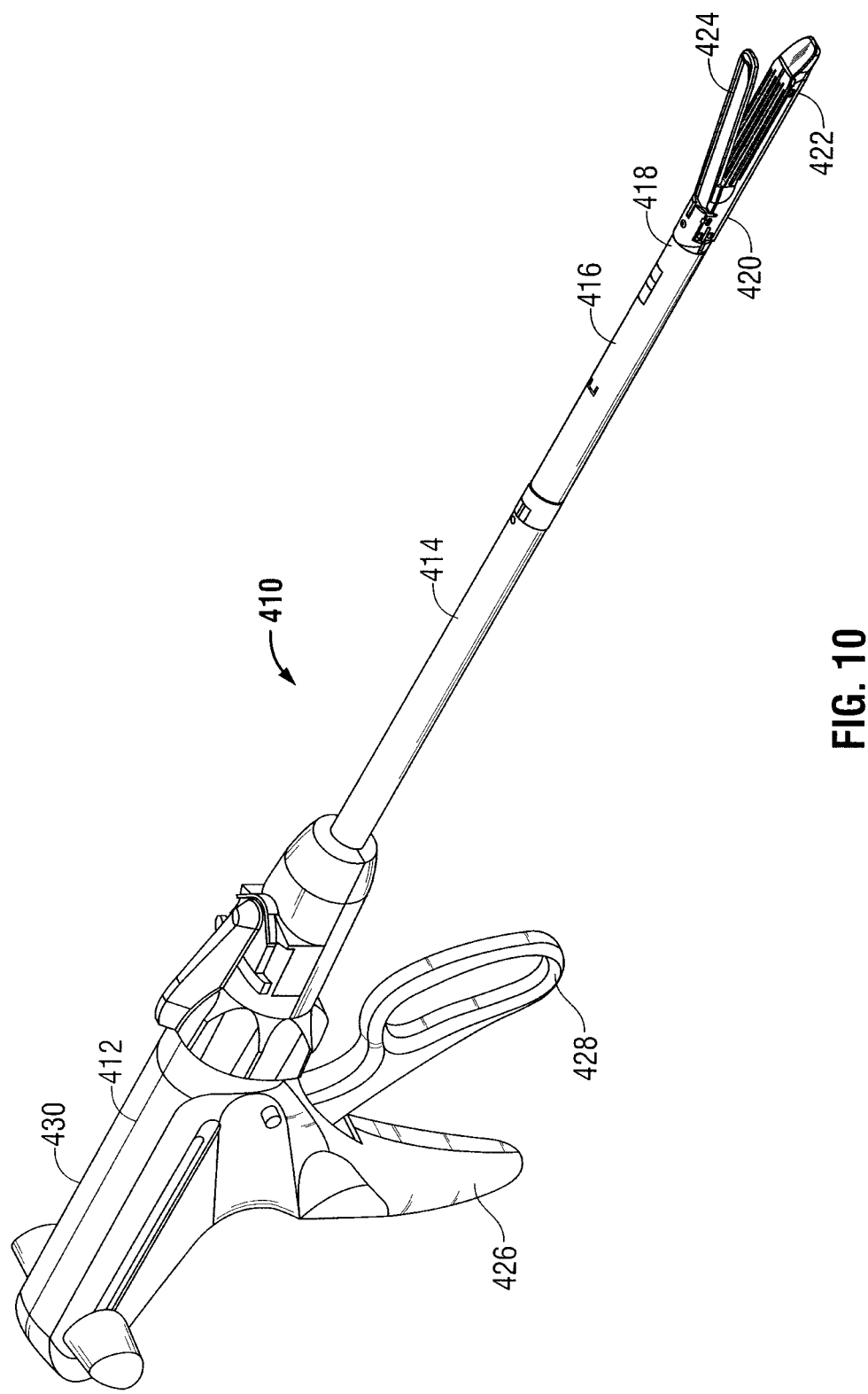
FIG. 10 is a perspective view of a medical instrument according to an embodiment of the disclosure.
Figure 11:
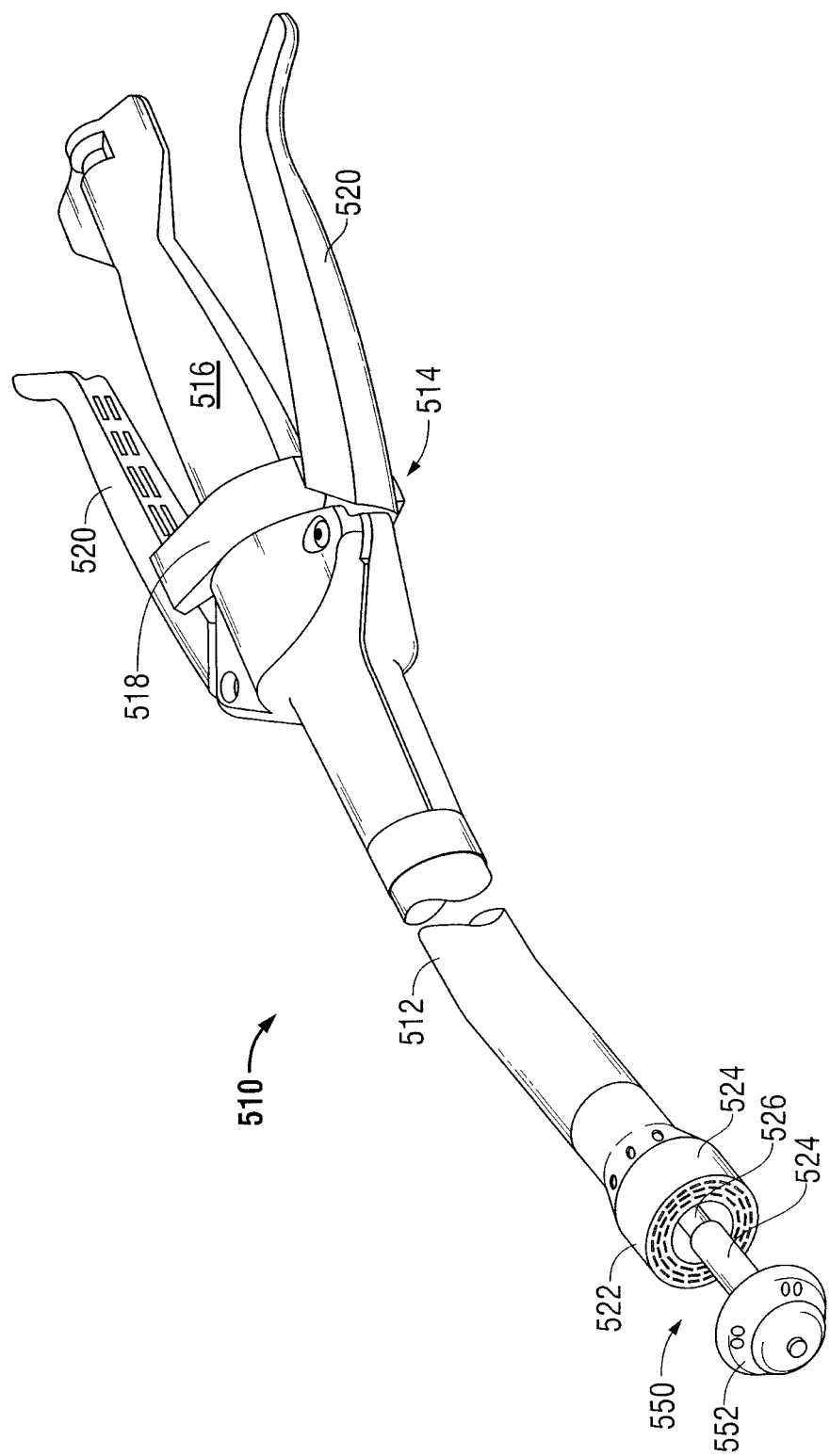
FIG. 11 is a perspective view of a medical instrument according to an embodiment of the disclosure.

FIGS. 10 and 11 illustrate other various stapling instruments suitable for deploying implantable repositories 200 within tissue. FIG. 10 shows a linear surgical stapling instrument 410, which is described in greater detail in a commonly-owned U.S. Patent Publication No. 2004/0232201, the entire disclosure of which is incorporated by reference herein. The stapling instrument 410 includes a handle assembly 412 and an elongated body 414. Handle assembly 412 includes a stationary handle member 426, a movable handle 428 and a barrel portion 430. The length of elongated body 414 may vary to suit a particular surgical procedure. A disposable end effector assembly or end effector assembly 416 is releasably secured to a distal end of elongated body 414. The end effector assembly 416 includes a proximal body portion 418, which forms an extension of elongated body 414, and a distal tool assembly 420 including a cartridge assembly 422 and an anvil assembly 424. Tool assembly 420 is connectable to body 418 about an axis substantially perpendicular to the longitudinal axis of elongated body 414. Cartridge assembly 422 houses a plurality of fasteners such as those illustrated in 100 or 110 (FIG. 3). Anvil assembly 424 is movable in relation to cartridge assembly 422 between an open position spaced from cartridge assembly 422 and an approximated or clamped position in juxtaposed alignment with cartridge assembly 424 in response to actuation of the handle assembly 412. Another suitable linear surgical stapling instrument is ENDO GIA™ available from Tyco Health Group LP, doing business as Covidien (North Haven, Conn.).

During operation, the anvil assembly 424 is closed about tissue relative to the cartridge assembly 422 by moving the movable handle 428 through an actuation stroke, which locks the anvil assembly 424 and the cartridge assembly 422 in position. Subsequent actuation of the movable handle 428 ejects the staples from the cartridge assembly 422, which are then deformed against the inner surface of the anvil assembly 422.

FIG. 11 shows a circular surgical stapling instrument 510, which is described in greater detail in a commonly-owned U.S. Pat. No. 5,758,814, the entire disclosure of which is incorporated by reference herein. The surgical instrument 510 is configured to apply a circular array of fasteners, e.g., staples, instrument 510 includes elongate body portion 512, proximal handle section 514 and distal fastener head portion 522. Handle section 514 includes anvil adjustment member 516, lever lockout or safety member 518 and fastener firing levers 520. Fastener head portion 522 includes annular staple cartridge 524 and movable anvil shaft connecting member 526. Anvil shaft connecting member 526 is longitudinally movable between a first, extended position and a second, retracted position. Pivotable anvil assembly 550 is shown spaced from fastener head portion 522 and includes anvil 552 secured to a distal portion of shaft 554. The proximal portion of shaft 556 is adapted to be secured to anvil shaft connecting member 526. During operation, the anvil assembly 550 and the head portion 522 are clamped about tissue via actuation of the adjustment member 516. The fasteners, such as those shown in 100 or 110 (FIG. 3), are fired via subsequent actuation of the firing levers 520, which causes the fasteners to be deformed against the inner surface of the anvil assembly 550.

Figure 12:
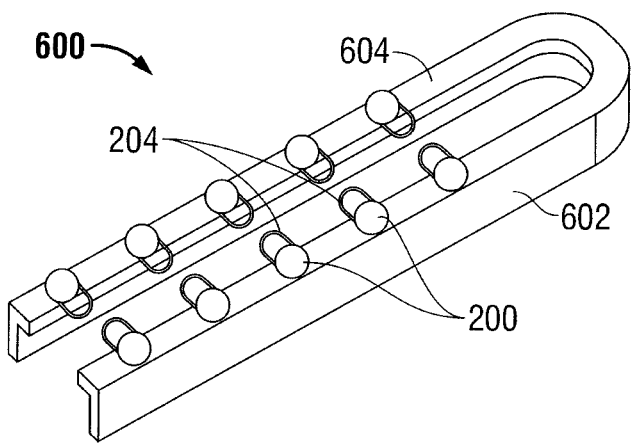
FIG. 12 is a perspective view of an implantable repository support assembly according to an embodiment of the disclosure.
Figure 13:
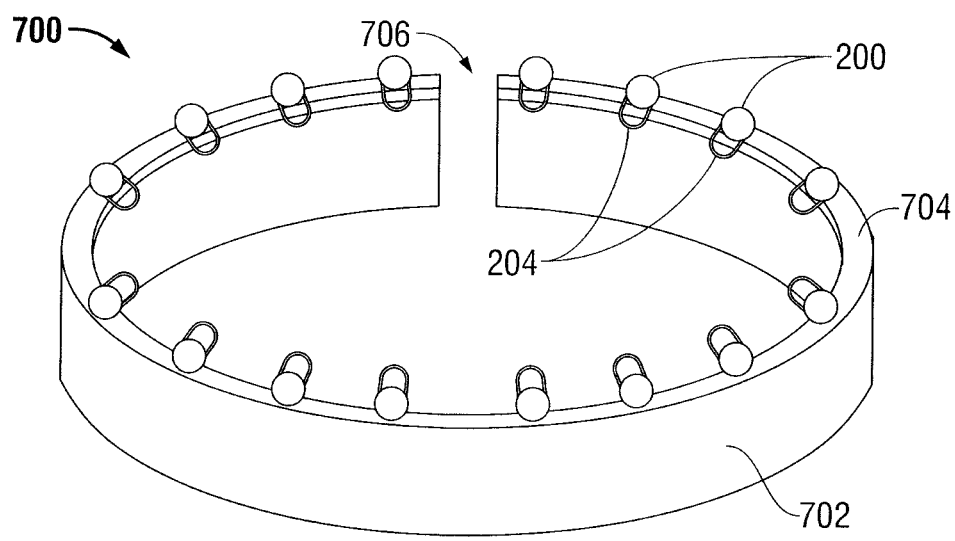
FIG. 13 is a perspective view of an implantable repository support assembly according to an embodiment of the disclosure.

FIGS. 12 and 13 illustrate implantable repository support assemblies 600 and 700, respectively, which may be used in combination with instruments 410 and 510. With respect to FIG. 12, the repository support assembly 600 includes a support member 602 and a working surface 604. The support member 602 may be formed from a resilient material, such as plastic or metal, and may be configured to engage either the cartridge assembly 422 or the anvil assembly 424. The repository support assembly 600 also includes a plurality of implantable repositories 200 disposed on the working surface 604 thereof. Since the repository support assembly 600 may be disposed on either or both of the cartridge assembly 422 or the anvil assembly 424, the working surface 604 is disposed between the cartridge and the anvil assemblies 422 and 424. The implantable repositories 200 are positioned with the attachment members 204 being in the firing path of the fasteners, allowing the implantable repositories 200 to be secured to the tissue as the fasteners are fired. More specifically, as the fasteners, such as 100 and 110 (FIG. 3) are ejected from the cartridge, the fastener legs 102, 104 of fastener 100 or 110a, 110b of fastener 110 (FIG. 3), are ejected therethrough the attachment member. The fasteners may be coupled with the repositories either before or after piercing tissue, prior to forming the final fastener shape, e.g., with the fastener legs bent inward. This allows the implantable repositories 200 to be attached to the medical device and/or tissue. Attachment to tissue may be on either side of the stapled surface or along any portion thereof, e.g., the implantable repositories 200 may be placed on the proximal, distal, left or right sides of the tissue.

With respect to FIG. 13, the repository support assembly 700 includes a support member 702 and a working surface 704. The support member 702 may be formed from a resilient material, such as plastic or metal. The support member includes a gap 706 to allow for fitting thereof around the staple cartridge 524. The repository support assembly 700 also includes a plurality of implantable repositories 200 disposed on the working surface 704 thereof. Since the repository support assembly 700 is disposed around the staple cartridge 524, the working surface 704 is disposed between the cartridge 524 and the anvil assembly 550, positioning the implantable repositories 200 with the attachment members in the firing path of the fasteners. Similar to FIG. 12, as the fasteners, such as 100 and 110 (FIG. 3) are ejected from the cartridge, the fastener legs 102, 104 of fastener 100 or 110a, 110b of fastener 110 (FIG. 3), are ejected therethrough the attachment member. The fasteners may be coupled with the repositories either before or after piercing tissue, prior to forming the final fastener shape, e.g., with the fastener legs bent inward.

Figure 14:
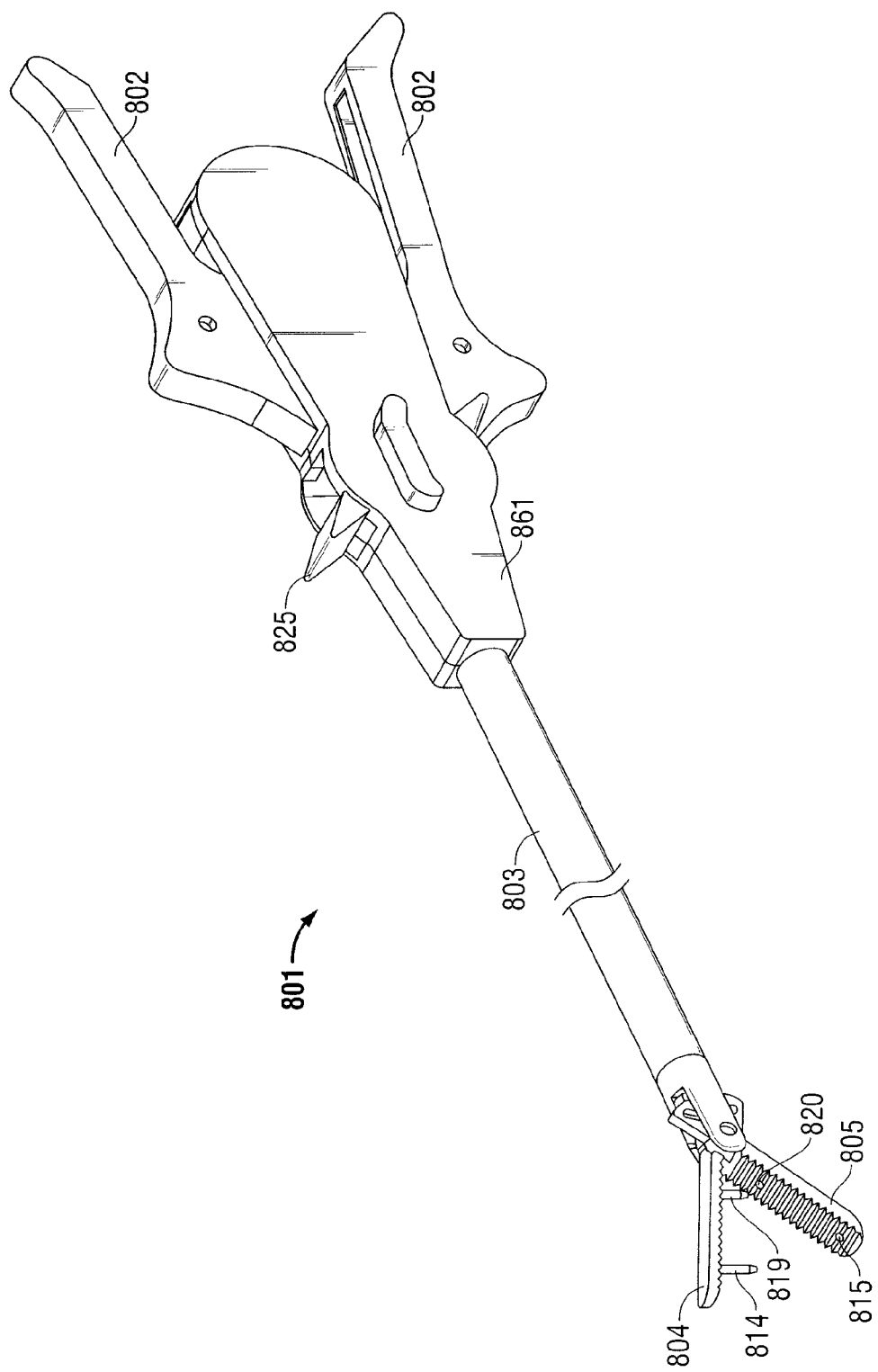
FIG. 14 is a perspective view of a medical instrument according to an embodiment of the disclosure.

In embodiments, the implantable repositories 200 may be attached to the medical devices or tissue using sutures which may be applied either manually or with the aid of a suturing instrument 801 shown in FIG. 14. The suturing instrument 801 includes a handle housing 861 with a two-armed handle 802, an elongated tubular housing or body portion 803, and two opposing jaw members 804 and 805. The handle 802 is used to control the opening and closing of jaw members 804 and 805 and may be designed to move in the same plane as the jaw members 804 and 805. Handle 802 may also be rotatably connected to body portion 803. This embodiment is particularly well-adapted for use in endoscopic or laparoscopic procedures as the tubular housing 803 may be dimensioned to be deployable through a tubular cannula structure, e.g., having internal diameter of from about 5 mm to about 10 mm.

Each jaw member 804 and 805 is adapted to receive a needle 814 in a recess 815. When jaw members 804 and 805 are closed, the needle 814 sits in the recess 815. Each jaw member 804 and 805 may also be adapted to hold a suture anchor 819 of a suture (not shown) while the other jaw member includes a recess 820 to accept the suture anchor 819. The distance between the needle's recess 815 and the anchor's recess 820 approximately equals the distance between the needle 814 and anchor 819 in the loading mechanism to facilitate proper loading. Suture anchor 819 can be fixedly attached to needle 814 by suture. Suture anchor 819 may also help guide and position needle 814 into recess 815. If anchor 819 is not properly placed in recess 820, jaw members 804 and 805 cannot close. If anchor 819 is properly placed, however, this placement helps guide the position of needle 814 into recess 815. Alternatively, a separate positioning element may be provided.

During operation of the suturing instrument 801, the jaws members 804 and 805 are positioned around the tissue to be sutured. Handles 802 are squeezed, closing the jaw members 804 and 805 around the tissue and piercing the tissue with needle 814, which is held securely in jaw 804. As needle 814 pierces the tissue, it is guided into a recess 815 in the opposite jaw member 805. Thereafter the needle 814 is released from jaw member 804 and is engaged in the jaw member 805. The needle 814 is then positioned in the jaw member 805, drawing the suture through the tissue. The anchor 819 rests on the tissue, thereby securing the suture in the tissue. The jaw members 804 and 805 are then opened by releasing the handles. The needle 814 may be double-pointed, allowing the instrument 801 to make another stitch. Further details of the suturing instrument 801 are described in a commonly-owned U.S. Pat. No. 5,728,107, the entire disclosure of which is incorporated by reference herein. In embodiments, any suturing instrument may also be used for securing the implantable repositories, such as ENDOS-TITCH™. available from Tyco Health Group LP, doing business as Covidien (North Haven, Conn.).

Suturing instrument 801 may be used to suture through attachment member of implant repository. For example, the needle 814 may be passed back and forth between jaw members, coupling the suture (not shown) to the repository. In other embodiments, the suturing instrument 801 may be provided with a loading unit (including needle and suture) having an implant repository attached thereto.

In embodiments, the medical instruments of the present disclosure for attaching the implantable repositories may be used in endoscopic procedures via single incision laparoscopic surgery access ports, such as SILS™ Ports, also available from Tyco Health Group LP, doing business as Covidien (North Haven, Conn.).

The repository may be fabricated from any biodegradable or non-biodegradable polymer. The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body such that the degradation products are excretable or absorbable by the body. Bioabsorbable materials are absorbed by biological tissues and disappear in vivo at the end of a given period, which can vary for example from hours to several months, depending on the chemical nature of the material. It should be understood that such materials include both natural and synthetic materials, as well as combinations thereof.

Suitable polymers which may be used to construct implants disclosed herein include, for example, synthetic materials, natural materials (e.g., biological) and combinations thereof. Suitable materials include, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers and copolymers, such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins, such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other to create a core of a fiber, for example a fiber possessing a core-sheath configuration.

Suitable bioabsorbable polymers may include implants of the present disclosure include, but are not limited to, polymers selected from the group consisting of aliphatic polyesters; polyamides; polyamines; polyalkylene oxalates; poly (anhydrides); polyamidoesters; copoly(ether-esters); poly (carbonates) including tyrosine derived carbonates; poly (hydroxyalkanoates) such as poly(hydroxybutyric acid), poly(hydroxyvaleric acid), and poly(hydroxybutyrate); polyimide carbonates; poly(imino carbonates) such as such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, for the purpose of this disclosure, aliphatic polyesters include, but are not limited to, homopolymers and copolymers of lactide (including lactic acid, D-, L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; .DELTA.-valerolactone; .beta.-butyrolactone; .gamma.-butyrolactone; .epsilon.-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; .alpha., .alpha. diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable biodegradable polymers include, but are not limited to, poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

The repositories may be prepared by any method within the purview of those skilled in the art, including, but not limited to, emulsion, double emulsion, extrusion, casting, molding, combinations thereof, and the like. In embodiments, the repositories may be formed in a mold designed to include an attachment member in the Rhin of a handle, hook, or the like.

The repository contains at least one bioactive agent which, in certain embodiments, may be disposed within the housing. The bioactive agent may be embedded within the polymer forming the repository, surrounded by the housing, coated on the housing, or otherwise integrated into the housing. In some embodiments the bioactive agent is disposed within the housing. In particular embodiments, the repository may comprise a hollow capsule, which is subsequently loaded or injected with a bioactive agent.

The term "bioactive agent," as used herein, is used in its broadest sense and includes any substance or mixture of substances that have clinical use. Consequently, bioactive agents may or may not have pharmacological activity per se, e.g., a dye. Alternatively a bioactive agent could be any agent, which provides a therapeutic or prophylactic effect, a compound that affects or participates in tissue growth, cell growth, cell differentiation, an anti-adhesive compound, a chemotherapeutic agent, an analgesic agent, a compound that may be able to invoke a biological action such as an immune response, or could play any other role in one or more biological processes.

Examples of classes of bioactive agents which may be utilized in accordance with the present disclosure, include, for example anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; antispasmodics; hormones; growth factors; muscle relaxants; adrenergic neuron blockers; antineoplastics; immunogenic agents; immunosuppressants; gastrointestinal drugs; diuretics; hemostatic agents; steroids; lipids; lipopolysaccharides; polysaccharides; platelet activating drugs; clotting factors; and enzymes. It is also intended that combinations of bioactive agents may be used.

Anti-adhesive agents can be used to prevent adhesions from forming between the hydrogel, in embodiments a hydrogel implant, and surrounding tissues. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents, which may be included as a bioactive agent include: triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides, such as tobramycin and gentamicin, rifampicin, bacitracin, neomycin, chloramphenicol, and miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent.

Other bioactive agents, which may be included as a bioactive agent include: local anesthetics; non-steroidal anti-fertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins; cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in the hydrogel include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (.beta.-IFN, .alpha.-IFN and .gamma.-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as anti-sense molecules, DNA, RNA, RNAi; oligonucleotides; polynucleotides; and ribozymes.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

What is claimed is:

1. A medical instrument comprising:
   an elongated shaft having a proximal end and a distal end;
   a handle assembly coupled to the proximal end of the elongated shaft, the handle assembly including a trigger; and
   an end effector assembly disposed at the distal end of the elongated shaft, the end effector assembly actuatable by the trigger and including:
      a cartridge assembly having at least one implantable repository; and
      an anvil assembly having a plurality of fasteners that are separate from the at least one implantable repository,
      wherein upon actuation of the trigger, at least one of the plurality of fasteners engages the at least one implantable repository and is ejected from the cartridge assembly along with the at least one implantable repository.

2. The medical instrument according to claim 1, wherein the at least one implantable repository includes:
   a capsule defining a housing having at least one enclosed lumen therein, the lumen having at least one bioactive agent disposed therein; and
   at least one loop attachment member coupled to the housing, the at least one attachment member configured to couple the implantable repository to at least one of the plurality of fasteners during firing thereof.

3. The medical instrument according to claim 2, wherein the housing comprises at least one biodegradable polymer.

4. The medical instrument according to claim 3, wherein the at least one biodegradable polymer is selected from the group consisting of aliphatic polyesters, polyamides, polyamines, polyalkylene oxalates, poly(anhydrides), polyamidoesters, copoly(ether-esters), poly(carbonates), poly(hydroxyalkanoates), polyimide carbonates, poly(imino carbonates), polyorthoesters, polyoxaesters, polyphosphazenes, poly(propylene fumarates), polyurethanes, polymer drugs, protein modified bioabsorbable polymers, and combinations thereof.

5. The medical instrument according to claim 2, wherein the at least one loop attachment member comprises a first end and a second end, wherein at least one of the first end or the second end is detachable from the housing.

6. The medical instrument according to claim 2, wherein the at least one bioactive agent is selected from the group consisting of an anesthetic agent, an antibiotic agent, an antimicrobial agent, an anticoagulant agent, a hemostatic agent, an anti-adhesive agent, a chemotherapeutic agent, an analgesic agent, and combinations thereof.

7. A medical instrument comprising:
   an elongated shaft; and
   a tool assembly disposed at a distal end of the elongated shaft, the tool assembly including:
      an anvil assembly;
      a cartridge assembly having a plurality of fasteners; and
      a repository support assembly selectively engageable with at least one of the anvil assembly or the cartridge assembly, the repository support assembly having at least one implantable repository disposed thereon, wherein the at least one implantable repository is separate from the plurality of fasteners and disposed in a firing path of the plurality of fasteners, such that the at least one implantable repository is coupled to at least one of the plurality of fasteners upon firing thereof.

8. The medical instrument according to claim 7, wherein the at least one implantable repository includes:
   a capsule defining a housing having at least one enclosed lumen therein, the lumen having at least one bioactive agent disposed therein; and at least one loop attachment member coupled to the housing, the at least one attachment member configured to couple the implantable repository to at least one of a plurality of fasteners.

9. The medical instrument according to claim 8, wherein the housing comprises at least one biodegradable polymer.

10. The medical instrument according to claim 9, wherein the at least one biodegradable polymer is selected from the group consisting of aliphatic polyesters, polyamides, polyamines, polyalkylene oxalates, poly(anhydrides), polyamidoesters, copoly(ether-esters), poly(carbonates), poly(hydroxyalkanoates), polyimide carbonates, poly(imino carbonates), polyorthoesters, polyoxaesters, polyphosphazenes, poly(propylene fumarates), polyurethanes, polymer drugs, protein modified bioabsorbable polymers, and combinations thereof.

11. The medical instrument according to claim 8, wherein the at least one loop attachment member comprises a first end and a second end, wherein at least one of the first end or the second end is detachable from the housing.

12. The medical instrument according to claim 8, wherein the at least one bioactive agent is selected from the group consisting of an anesthetic agent, an antibiotic agent, an antimicrobial agent, an anticoagulant agent, a hemostatic agent, an anti-adhesive agent, a chemotherapeutic agent, an analgesic agent, and combinations thereof.

13. The medical instrument according to claim 7, wherein the anvil assembly is movable relative to the cartridge assembly.

14. The medical instrument according to claim 13, wherein the anvil assembly is movable relative to the cartridge assembly along a longitudinal axis defined by the elongated shaft.

15. The medical instrument according to claim 14, wherein the anvil assembly is rotatable relative to the cartridge assembly about a pivot axis that is perpendicular to a longitudinal axis defined by the elongated shaft.

* * * * *